US010968027B2

(12) United States Patent
Wang

(10) Patent No.: US 10,968,027 B2
(45) Date of Patent: Apr. 6, 2021

(54) APPARATUS, ARRANGEMENT AND METHOD FOR PROVIDING SKIN CARE INGREDIENTS

(71) Applicant: MEMORIAL SLOAN-KETTERING CANCER CENTER, New York, NY (US)

(72) Inventor: Steven Wang, Chatham, NJ (US)

(73) Assignee: MEMORIAL SLOAN-KETTERING CANCER CENTER, New York, NY (US)

( * ) Notice: Subject to any disclaimer, the term of this patent is extended or adjusted under 35 U.S.C. 154(b) by 0 days.

(21) Appl. No.: 16/284,870

(22) Filed: Feb. 25, 2019

(65) Prior Publication Data

US 2019/0193915 A1    Jun. 27, 2019

Related U.S. Application Data

(62) Division of application No. 14/900,941, filed on Dec. 22, 2015, now Pat. No. 10,214,339.

(Continued)

(51) Int. Cl.
*B65D 25/08* (2006.01)
*B65D 81/32* (2006.01)
(Continued)

(52) U.S. Cl.
CPC ....... *B65D 81/3266* (2013.01); *A45D 44/002* (2013.01); *A61K 8/022* (2013.01);
(Continued)

(58) Field of Classification Search
CPC ............. B65D 81/3266; B65D 25/082; B65D 51/2857; B65D 75/5805; B65D 2203/12;
(Continued)

(56) References Cited

U.S. PATENT DOCUMENTS 5,616,337 A * 4/1997 Kasianovitz ....... B65D 81/3266
424/414
6,286,670 B1    9/2001 Smith
(Continued)

FOREIGN PATENT DOCUMENTS

CN    102574645 A    7/2012
JP    2000-288066 A    10/2000
(Continued)

OTHER PUBLICATIONS

Notice of Reasons for Rejection dated Sep. 4, 2018 for Japanese patent Application No. 2016-524316.
(Continued)

*Primary Examiner* — Luan K Bui
(74) *Attorney, Agent, or Firm* — Hunton Andrews Kurth LLP

(57) ABSTRACT

According to an exemplary embodiment of the present disclosure, a cosmetic arrangement can be provided, which can include a first structure that can enclose a cosmetic active ingredient(s), a second structure that can enclose a solvent solution, a third structure(s) that can separate the solvent solution from the cosmetic active ingredient(s), a medium that can be configured to absorb a mixture of the cosmetic active ingredient(s) and solvent solution, and an indicator structure that can be configured to indicate whether the cosmetic active ingredient(s) and the solvent solution have come in contact with one another. Upon an application of a particular amount of pressure on a portion(s) of the arrangement, the cosmetic active ingredient(s) and the solvent solution can be caused to come into direct contact with one another.

10 Claims, 15 Drawing Sheets

Related U.S. Application Data

(60) Provisional application No. 61/842,144, filed on Jul. 2, 2013, provisional application No. 62/010,044, filed on Jun. 10, 2014.

(51) Int. Cl.
| | |
|---|---|
| *A61K 8/67* | (2006.01) |
| *B65D 75/58* | (2006.01) |
| *A61K 8/02* | (2006.01) |
| *A45D 44/00* | (2006.01) |
| *A61Q 19/08* | (2006.01) |
| *B65D 79/02* | (2006.01) |
| *B65D 41/02* | (2006.01) |
| *A45D 34/00* | (2006.01) |

(52) U.S. Cl.
CPC ............ *A61K 8/0212* (2013.01); *A61K 8/676* (2013.01); *A61K 8/678* (2013.01); *A61Q 19/08* (2013.01); *B65D 25/082* (2013.01); *B65D 41/02* (2013.01); *B65D 75/585* (2013.01); *B65D 75/5805* (2013.01); *B65D 75/5855* (2013.01); *B65D 79/02* (2013.01); *A45D 34/00* (2013.01); *A45D 2200/058* (2013.01); *A45D 2200/1036* (2013.01); *A61K 2800/882* (2013.01); *B65D 2203/12* (2013.01)

(58) Field of Classification Search
CPC .. B65D 41/02; B65D 75/585; B65D 75/5855; B65D 79/02; A45D 34/00; A45D 44/002; A45D 2200/1036; A45D 2200/058; A61K 8/0212; A61K 8/676
USPC ................................ 206/219–222, 568, 581
See application file for complete search history.

(56) References Cited

U.S. PATENT DOCUMENTS

| | | | | |
|---|---|---|---|---|
| 6,945,402 | B1* | 9/2005 | Gueret | ............... B65D 81/3272 206/219 |
| 7,357,248 | B2* | 4/2008 | Sivakumar | .............. A47L 13/17 206/219 |
| 8,100,294 | B2 | 1/2012 | May et al. | |
| 8,881,894 | B2* | 11/2014 | Castel | .................. A61K 31/375 206/219 |
| 9,415,919 | B2 | 8/2016 | Kuribayashi | |
| 2003/0206878 | A1 | 11/2003 | Gott et al. | |
| 2004/0112769 | A1 | 6/2004 | Perry | |
| 2006/0054634 | A1 | 3/2006 | Mekata | |
| 2006/0239957 | A1 | 10/2006 | Lintner | |
| 2007/0138033 | A1 | 6/2007 | Cho | |
| 2009/0081266 | A1 | 3/2009 | Ying et al. | |
| 2009/0247575 | A1 | 10/2009 | Asotra et al. | |
| 2010/0140119 | A1 | 6/2010 | Katsuki | |
| 2010/0236951 | A1 | 9/2010 | Huff et al. | |
| 2011/0100844 | A1 | 5/2011 | Cimaglio et al. | |

FOREIGN PATENT DOCUMENTS

| | | |
|---|---|---|
| JP | 2002-543009 A | 12/2002 |
| JP | 2007-112482 A | 5/2007 |
| WO | 2011056442 A1 | 5/2010 |

OTHER PUBLICATIONS

Third Chinese Office Action dated Sep. 5, 2018 for Chinese National phase application No. 201480044035.3.
International Search Report for International Patent Application No. PCT/US2014/045066 dated Nov. 7, 2014.
International Written Opinion for International patent Application No. PCT/US2014/045066 dated Nov. 7, 2014.
Second Office Action for Chinese National Phase Application No. 201480044035.3 dated Nov. 29, 2017.
"The Secret of Cosmetic Packaging," Environment Education, Issue No. 6, pp. 82-83, Jun. 25, 2010.
Notification of the First Office Action dated Mar. 17, 2017 for Chinese National Phase Application No. 201480044035.3.
Decision of Rejection dated May 7, 2019 for Japanese patent application No. 2016-524316.

* cited by examiner

APPARATUS, ARRANGEMENT AND METHOD FOR PROVIDING SKIN CARE INGREDIENTS

CROSS-REFERENCE TO RELATED APPLICATIONS

The present application a divisional of relates to and claims the benefit and priority from U.S. application Ser. No. 14/900,941 filed on Dec. 22, 2015, which is a national phase of International Patent Application No, PCT/US2014/045066 filed on Jul. 1, 2014 that was published on Jan. 8, 2015 as International Publication No, WO 2015/002960, which relates to U.S. Patent Application Nos. 61/842,144, filed on Jul. 2, 2013 and 62/010,044 filed on Jun. 10, 2014, the entire disclosures of which are incorporated herein by reference.

FIELD OF THE DISCLOSURE

The present disclosure relates generally to skin care or cosmetic ingredients. More specifically, to exemplary embodiments of an arrangement, apparatus and method that can provide the skin care ingredients via a package arrangement that can include a burstable and/or breakable compartment which can store active and/or non-active ingredients, such as, for example, skin care related ingredients.

BACKGROUND INFORMATION

Cosmetic products, such as cosmetic masks, can be widely used to deliver various health and cosmetic benefits to the skin, such as on the face, neck and chest.

Traditionally, the masks can be sold commercially in packaged bags with the various active ingredients (e.g., green tea extract, vitamin A, vitamin C, vitamin E, resveratrol, Q10, and/or other similar ingredients) already predisposed on the mask. For example, traditionally, the mask can generally be packaged already immersed in a liquid mixture, for example, the solvent, containing various active ingredients, for example, the solute. To use such mask, the user opens the package, removes the mask already pre-immersed in the liquid mixture and applies the mask to various parts of the body as instructed on the package.

The active ingredients dissolved in the liquid mixture can be delivered onto the skin using the mask achieve certain desired benefits. However, these traditional, and currently designed, pre-packaged masks deliver no or very little active cosmetic ingredients onto the skin. This is because the active ingredients, which can be dissolved in the liquid solution, become unstable, and can rapidly lose their activity over a short period of time (e.g., a few weeks). For example, Vitamin C (e.g., L-ascorbic acid) and Vitamin E (e.g. tocopherol) dissolved in a liquid solution and stored in a closed and dark container lose nearly 72% and 35%, respectively, of their initial activity after only 60 days. Exemplary results illustrating this loss as shown in FIGS. 1A and 1B. As a result, the active ingredient on the mask has little to no effectiveness by the time the packaged mask reaches the hands of the consumer as it can take weeks or months between the times the ingredients are dissolved and when the user applies the mask. This reduction in effectiveness can be further exacerbated if the packaged mask sits on the store shelf for a prolonged period of time or may not be immediately used by the user at the time of purchase.

Thus, there is a need for a packaged mask is which the active ingredient and solvent can be separated such that the active ingredients do not lose or do not significantly lose their effectiveness or activity before arriving at the hands of the consumer, and/or away to determine whether the active ingredients have been already mixed prior to use.

SUMMARY OF EXEMPLARY EMBODIMENTS

These and other objects of the exemplary embodiments of the present disclosure can be achieved by providing exemplary arrangement, apparatus and method which can provide the skin care ingredients via a package arrangement.

According to an exemplary embodiment of the present disclosure, a cosmetic arrangement can be provided, which can include a first structure that can enclose a cosmetic active ingredient(s), a second structure that can enclose a solvent solution, third structure(s) that can separate the solved solution from the cosmetic active ingredient(s), a medium that can be configured to absorb a mixture of the cosmetic active ingredient(s) and solvent solution, and an indicator structure that can be configured to indicate whether the cosmetic active ingredient(s) and the solvent solution have come in direct contact with one another. Upon an application of a particular amount of pressure on a portion(s) of the arrangement, the cosmetic active ingredient(s) and the solvent solution can be caused to come into direct contact with one another.

The first, second and third structures can form a single unitary structure with the third structure provided between the first and second structures. Pressure can be applied against the first structure or the second structure and can cause the third structure(s) to rupture so as to expose the cosmetic active ingredient(s) to the solvent solution, and mix the cosmetic active ingredient(s) with the solvent solution. The first, structure can include the indicator structure, and a portion(s) of the indicator structure can visible from an exterior of the first structure.

In some exemplary embodiments of the present disclosure, the second structure can be contained within the first structure, and the second structure can further comprise the third structure(s), wherein, upon the application of the pressure against the second structure, the third structure(s) ruptures thereby causing the solvent solution to be expelled from the second structure and come into direct contact with the cosmetic ingredient(s) in the first structure. The amount of the pressure applied on the second structure can be between approximately 0.2 lbs. approximately 5 lbs. The medium can absorb the mixture of the cosmetic active ingredient(s) and solvent solution after the third arrangement(s) can rupture.

The exemplary medium can include a mask that can be configured to be applied onto skin. The exemplary medium can include a face mask that can be configured to be applied onto a face.

The exemplary indicator structure comprises a pH agent that can be associated with the cosmetic active ingredient(s) and the solvent solution. When the cosmetic active ingredient(s) and the solvent solution come into direct contact with each other, the pH agent can change color. In some exemplary configurations of the present disclosure, the exemplary indicator structure can include a non-toxic and non-hazardous agent that can react with the mixture of the cosmetic active ingredient(s) and the solvent solution upon a contact therewith, and can produce an indication that the cosmetic active ingredient(s) and the solvent solution have been mixed.

The exemplary arrangement can further include a clear window area on the first structure that can facilitate an external view of an interior space of the first structure. The first structure can be substantially opaque to prevent or reduce an amount of light exposure to the cosmetic active ingredient(s) and the solvent solution.

In some exemplary embodiments of the present disclosure, the exemplary cosmetic active ingredient(s) can include an anti-oxidant. The cosmetic active ingredient(s) can be Vitamin E, Vitamin C, Vitamin A, selenium, Silymarin, polyphenols, polypodium leucotomos, green tea polyphenols, coenzyme Q10, Reservatrol, glutathione, flavonoids, peptides, retinol, sirtulins, ceremides, caffeine, alpha-lipoic acid, salicyclic acid, glycolic acid, alpha-hydroxy acid, hyaluronic acid, arbutin, licorice extract, kojic acid, ferulic acid, niacinamide, curcuminoids, isoflavones and the like. The solvent solution can be an aqueous solution and the cosmetic active ingredient(s) can be water-soluble (e.g., a water-soluble anti-oxidant). In some exemplary embodiments of the present disclosure, the solvent solution can be a lipid solution and the cosmetic active ingredient(s) can be fat-soluble (e.g., a fat-soluble anti-oxidant).

According to an exemplary method of applying a cosmetic product to a user's skin, the method can include providing an arrangement that can have a first structure that can enclose cosmetic active ingredient(s) and a medium that can be configured to absorb a mixture of the cosmetic active ingredient(s) and a solvent solution, a second structure that can be contained within the first structure and can enclose the solvent solution, a third structure(s) that can separate the solvent solution from the cosmetic active ingredient(s), and an indicator structure that can be configured to indicate whether the cosmetic active ingredient(s) and the solvent solution have come in direct contact with one another. The method can further include applying a particular amount of pressure against, a portion(s) of the second structure such that the second structure can cause the third structure(s) to rupture so as to expose the solvent solution to the cosmetic active ingredient(s), opening the first structure, removing the medium from the first structure; and applying the medium onto skin.

The exemplary method can further include facilitating the first structure to be shaken before opening thereof to facilitate the mixing of the cosmetic active ingredient(s) and the solvent solution and the absorption of the mixture of the cosmetic active ingredient(s) and solvent solution by the medium. The cosmetic active ingredient(s) can include an active cosmetic ingredient (e.g., an anti-oxidant). The cosmetic active ingredient(s) can be: Vitamin E, Vitamin C, Vitamin A, selenium, Silymarin, polyphenols, polypodium leucotomos, green tea polyphenols, coenzyme Q10, Reservatrol, glutathione, flavonoids, peptides, retinol, sirtulins, ceremides, caffeine, alpha-lipoic acid, salicyclic acid, glycolic acid, alpha-hydroxy acid, hyaluronic acid, arbutin, licorice extract, kojic acid, ferulic acid, niacinamide, curcuminoids, isoflavones and the like.

The solvent solution can be an aqueous solution, and the cosmetic active ingredient(s) can be water-soluble (e.g., a water-soluble anti-oxidant). In the solvent solution can be a lipid solution and the cosmetic active ingredient(s) can be fat-soluble (e.g., a fat-soluble anti-oxidant). In certain exemplary embodiments of the present disclosure, the solvent solution can be an aqueous-based solution that can contain emulsifiers that can dissolve both water-soluble and fat-soluble active cosmetic ingredients (e.g., anti-oxidants)

According to a further exemplary embodiment of the present disclosure, the arrangement can include a first structure that can enclose a cosmetic active ingredient(s), a second structure that can enclose a solvent solution, a medium that can be configured to absorb a mixture of the cosmetic active ingredient(s) and the solvent solution, and an indicator structure that can be configured to indicate whether the cosmetic active ingredient(s) and the solvent solution have some in direct contact with one another. Upon an application of a particular amount of pressure on a portion(s) of each of the first structure and the second structure, the cosmetic active ingredient(s) and the solvent solution can be caused to come into direct contact with one another.

According to an exemplary method of applying a cosmetic product to a user's skin, the method can include, for example, providing an arrangement having a first structure enclosing (i) a second rigid structure enclosing a first ingredient(s), (ii) a second ingredient(s) and (iii) a medium configured to absorb a mixture of the first ingredient(s) and the second ingredient(s). A particular amount of pressure can be applied against a portion(s) of the second rigid structure such that the first ingredient(s) and one second(s) ingredient can be caused to come into contact with one another. The first structure can be opened, and the medium can then be applied to the skin, for example, the free of a user.

In some exemplary embodiments of the presets disclosure, the first structure can be shakes to mix the first ingredient(s) and the second ingredient(s) and to cause an absorption of a mixture of the first ingredient(s) and the second ingredient(s) by the medium. The first ingredient(s) can include Vitamin E, Vitamin C, Vitamin A, selenium, Silymarin, polyphenols, polypodium leucotomos, green tea polyphenols, coenzyme Q10, Reservatrol, glutathione, flavonoids, peptides, retinol, sirtulins, ceremides, caffeine, alpha-lipoic acid, salicyclic acid, glycolic acid, alpha-hydroxy acid, hyaluronic acid, arbutin, licorice extract, kojic acid, ferulic acid, niacinamide, curcuminoids, and isoflavones.

Is certain exemplary embodiments of the present disclosure, the first ingredient(s) can be Vitamin E, Vitamin C, Vitamin A, selenium, Silymarin, polyphenols, polypodium leucotomos, green tea polyphenols, coenzyme Q10, Reservatrol, glutathione, flavonoids, peptides, retinol, sirtulins, ceremides, caffeine, alpha-lipoic acid, salicyclic acid, glycolic acid, alpha-hydroxy-acid, hyaluronic acid, arbutin, licorice extract, kojic acid, ferulic acid, niacinamide, curcuminoids, or isoflavones. The second ingredient(s) can be an aqueous solution, and the first ingredient(s) can be water-soluble. In some exemplary embodiments of the present disclosure, the second ingredient(s) can be a lipid solution, and the first ingredient(s) can be fat-soluble. In certain exemplary embodiments of the present disclosure, the first ingredient(s) can be an aqueous solution, and the second ingredient(s) can be water-soluble. In certain exemplary embodiments of the present disclosure, the first ingredient(s) can be a lipid solution, and the second ingredient(s) can be fat-soluble.

These and other objects, features and advantages of the exemplary embodiments of the present disclosure will become apparent upon reading the following detailed description of the exemplary embodiments of the present disclosure, when taken in conjunction with the appended exemplary claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1A:
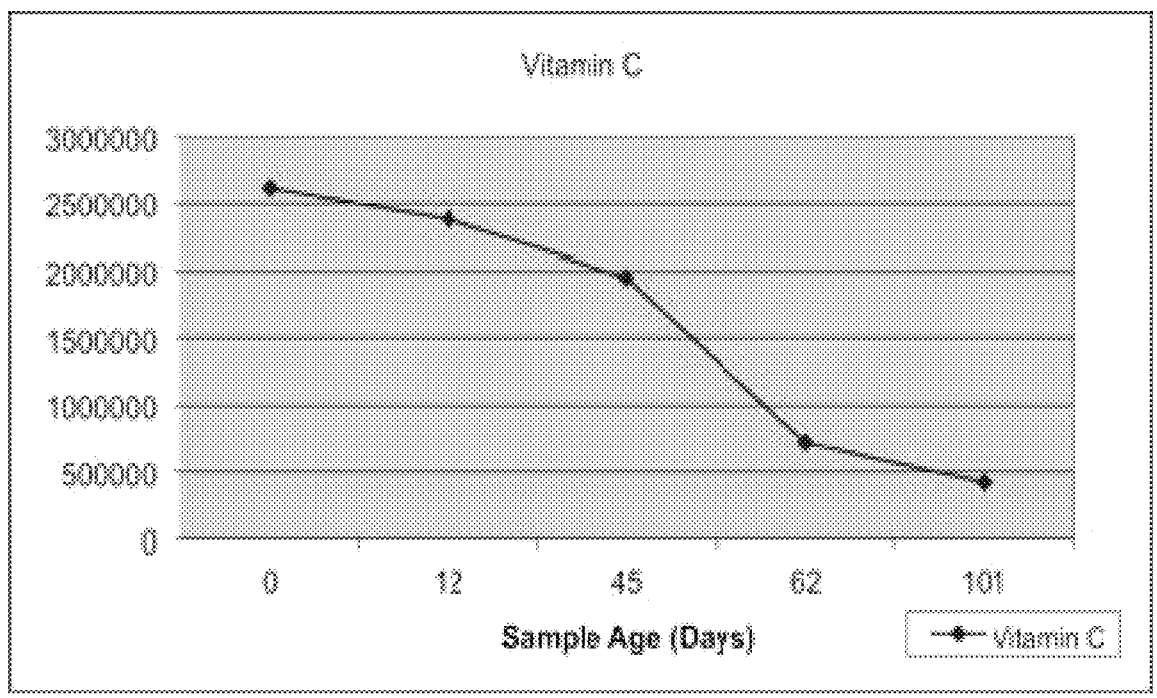
FIG. 1A is a graph of Decay rate of Vitamin C stored in liquid solution.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures or the appended claims.

DETAILED DESCRIPTION OF EXEMPLARY EMBODIMENTS

The arrangement, apparatus and method according to exemplary embodiments of the present disclosure may be further understood with reference to the following description and the related appended drawings. The arrangement, apparatus and method according to exemplary embodiments are described with reference to a cosmetic face mask arrangement and a method of applying the cosmetic face mask arrangement, although those having ordinary skill in the art will understand that the exemplary embodiments of the present disclosure can be implemented on other types of cosmetic arrangements.

The exemplary arrangement, according to an exemplary embodiment of the present disclosure, described herein can include a cosmetic arrangement 110 that can include a stable concentration of active ingredients that, for example, does not significantly degrade before arriving at the hands of the consumer.

The exemplary cosmetic arrangement 110 can include one or more solutes and one or more solvents that can be packaged separately and/or mixed by the user prior to using the cosmetic arrangement 110. As described in further detail herein, a solvent solution can be provided and contained in an exemplary burnable structure, such, as, for example, a pouch 114, within a packaging structure 112, and the packaging structure 112 can contain a solvent. Prior to use, the user can break the pouch 114 to cause the solvent to mix with the solvent within the packaging structure 112 by, for example, pressing on the pouch with a particular amount of pressure. The pouch can also be broken or torn by other ways. This can prevent a significant degradation of the solute, for example, cosmetic active ingredient, before being used by the user or others. Additional exemplary details of the exemplary cosmetic arrangement 110 are described in further detail herein.

The solute can be a cosmetic active ingredient, or a mixture of cosmetic active ingredients. Such cosmetic active ingredient(s) can include, but is not limited, Vitamin E, Vitamin C, Vitamin A, selenium, Silymarin, polyphenols, polypodium leucotomos, green tea polyphenols, coenzyme Q10, Reservatrol, glutathione, flavonoids, peptides, retinol, sirtulins, ceremides, caffeine, alpha-lipoic acid, salicyclic acid, glycolic acid, alpha-hydroxy acid, hyaluronic acid, arbutin, licorice extract, kojic acid, ferulic acid, niacinamide, curcuminoids, isoflavones, and the like. Additionally, the exemplary cosmetic ingredient can include any suitable anti-aging ingredient or any suitable anti-oxidant. The exemplary solute can be in the form of a powder, a liquid solution, one or more solid pellets or any other suitable form. For example, the solute can be in the form of a powder, or solid pellet(s), as such compositions can be more inert, and can retain its stability better than a liquid solution. The solvent can be an aqueous or lipid liquid solution, such as water or oil, depending on the solubility of the active ingredients. For example, if the active ingredient can be Vitamin E, the solvent can be oil-based because Vitamin E can be fat soluble. It is appreciated that other types of solvents can be used.

The average volume of liquid, including the solvent and solute solution, within the cosmetic arrangement 110 can be about 5 milliliters to about 40 milliliters. For example, in some configurations, the average volume of liquid, including the solvent and solute solution, can be about 10 milliliters to about 15 milliliters, however other suitable volume of liquid, including the solvent and solute solution, within the cosmetic arrangement 110 can be used.

Figure 2A:
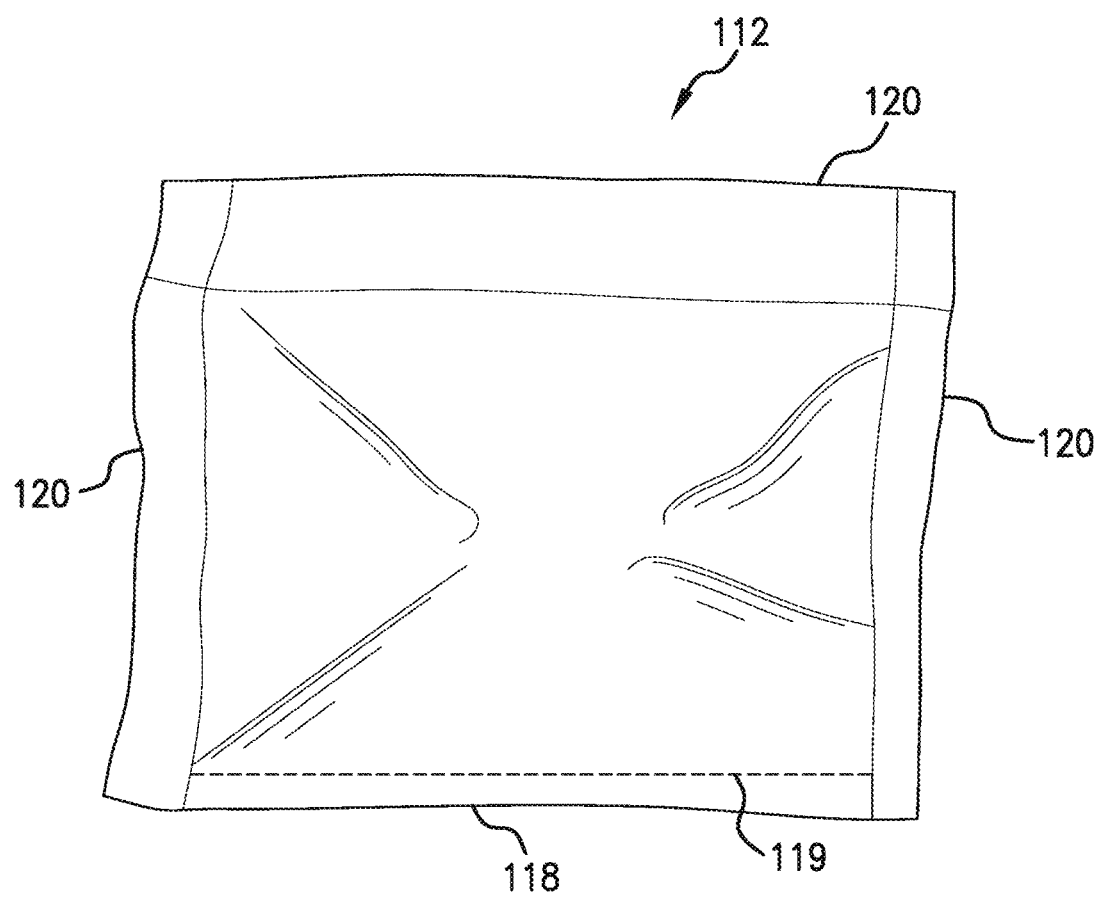
FIG. 2A is an illustration of the exemplary packaging structure in an unopened state according to an exemplary embodiment of the present disclosure.
Figure 2B:
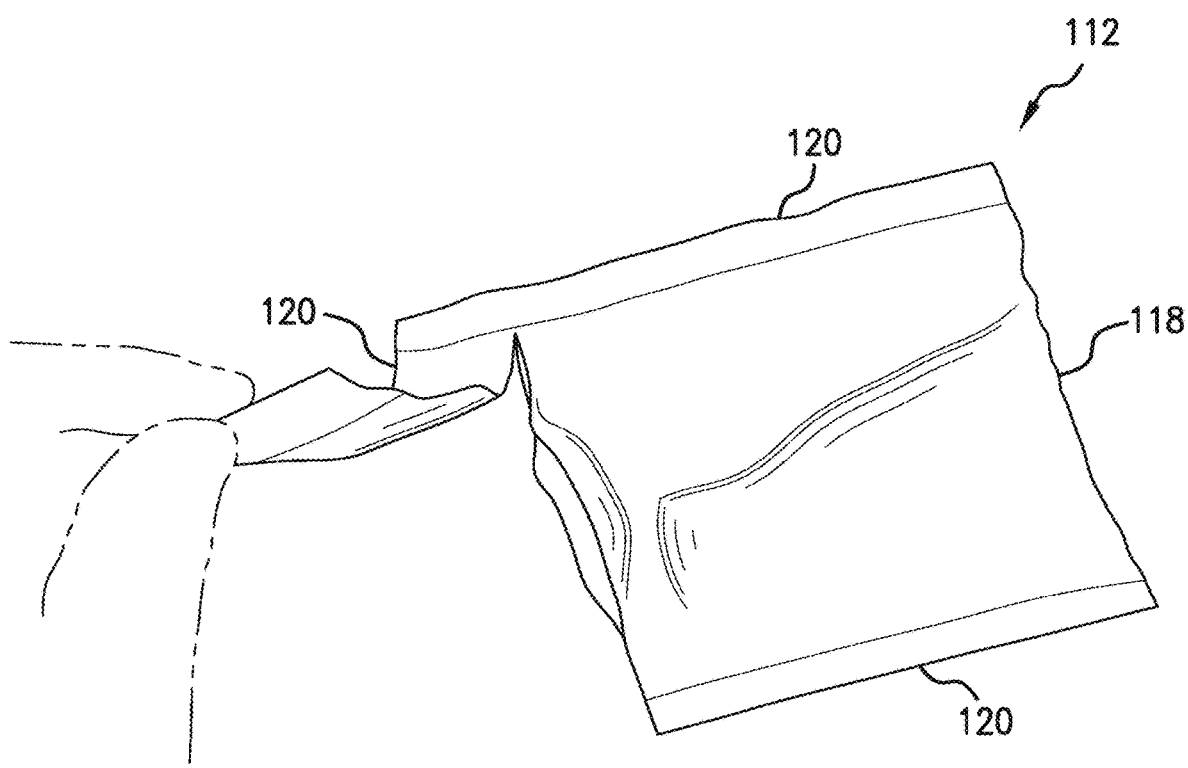
FIG. 2B is an illustration of the exemplary packaging structure after if has been opened according to an exemplary embodiment of the present disclosure.

The exemplary packaging structure 112, as also illustrated in FIGS. 2A and 2B, can be made of, for example, a single panel that can be C-folded to form a folded edge 118, and sealed along remaining edges 120 to form an interior space inside the packaging structure 112. Alternatively or in addition, the packaging structure 112 can be made of two panels that can be sealed together along all of the edges to form the interior space. The exemplary packaging structure 112 can be sufficiently large enough to store both the pouch 114 and the medium 116 within its interior space.

The packaging structure 112 can include a separation arrangement which can be more easily detachable (e.g., a line of weakness (119)) proximate al least one edge of the packaging structure, for example, the top edge opposite the folded edge 118. Alternatively, the separation arrangement can be positioned proximate other edges 120 of the packaging structure 112. The separation arrangement can be perforations that can be disposed proximate at least one edge 120, and can extend along such edge 120. In other exemplary configurations, the line of weakness 122 can be a small slit on at least one of the edges 120 that can extend inwardly, but may not extend info the interior space. As illustrated in FIG. 2B, the separation arrangement, which can include the perforation(s), small slit(s), or the like, can act as a starting point for the user to tear open the sealed bag and retrieve the contents, for example, the pouch 114 and the medium 116, within the interior space.

The packaging structure 112 can also include the cosmetic active ingredient(s), which can be packaged separately from the solvent. This can facilitate the medium 116 within the packing structure 112 to be exposed to the cosmetic active ingredient(s), but not the solvent solution. The packaging structure 112 can be substantially opaque which can prevent or significantly reduce the light exposure of the cosmetic active ingredient and the solvent solution. This can prevent the cosmetic active ingredients from significantly degrading before use.

Figure 1B:
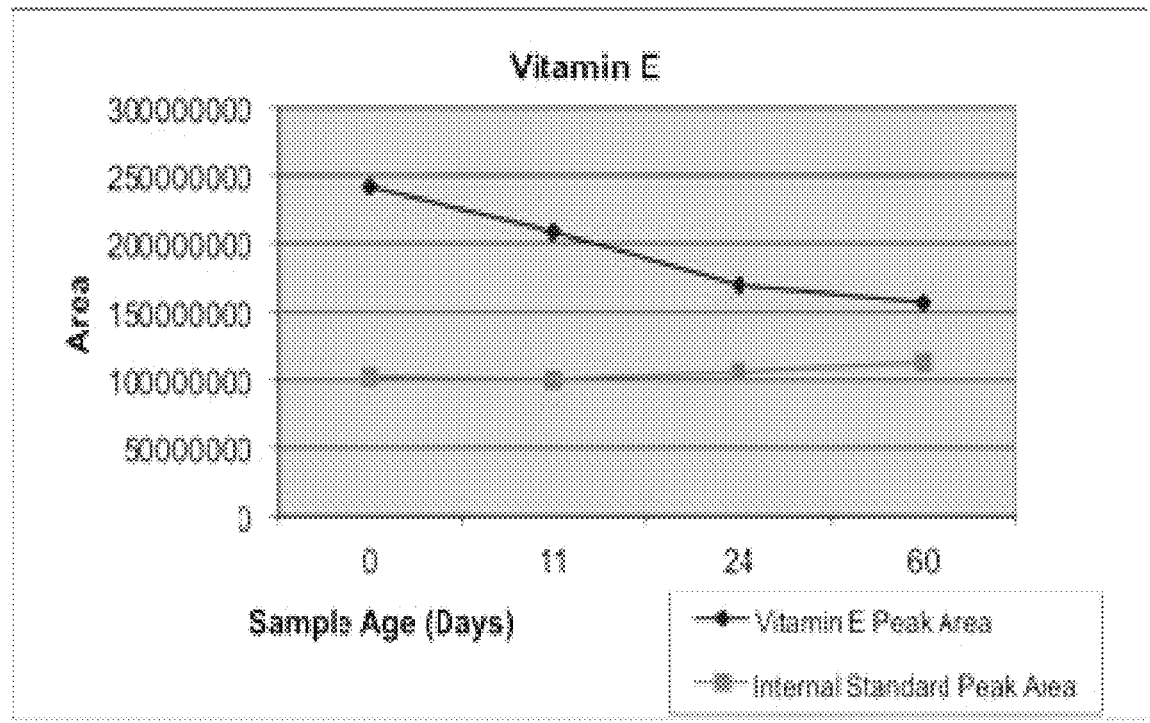
FIG. 1B is a graph of Decay rate of Vitamin E stored in liquid solution.
Figure 1C:
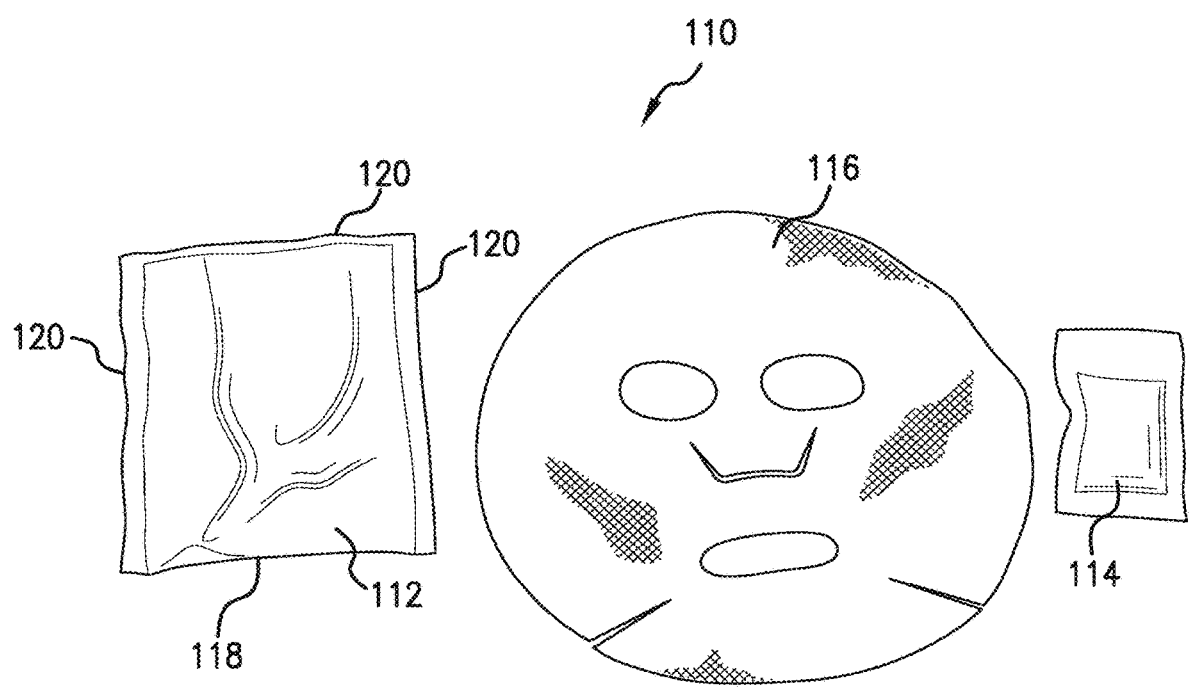
FIG. 1C is an illustration of an exemplary cosmetic arrangement which can include packaging structure (e.g., including ingredients), medium, and burstable structure according to an exemplary embodiment of the present disclosure.

Referring to FIG. 1, the cosmetic arrangement 110 can also include an exemplary medium 116 (e.g., a mask) that can act as a delivery vehicle for the various cosmetic active ingredients. The exemplary medium 116 can be made of a material such as paper, cotton fabric, cellulous and/or hydrogel, which can be configured to absorb the mixture of the cosmetic active ingredients and solvent solution, and deliver this mixture to a person's skin. As described above, the cosmetic active ingredient and medium 116 can both be contained in the packaging structure 112. In certain exemplary configurations, the cosmetic active ingredient can be packaged loosely, such as in a powdered form, with the exemplary medium 116 being provided in the packaging structure. In other exemplary configurations, the medium 116 can already have the cosmetic active ingredients infused or absorbed into the medium material during the manufacturing process or during packaging of the medium 116 such that there can be little to no loose particles of the cosmetic active ingredient within the packaging structure 112.

Figure 3:
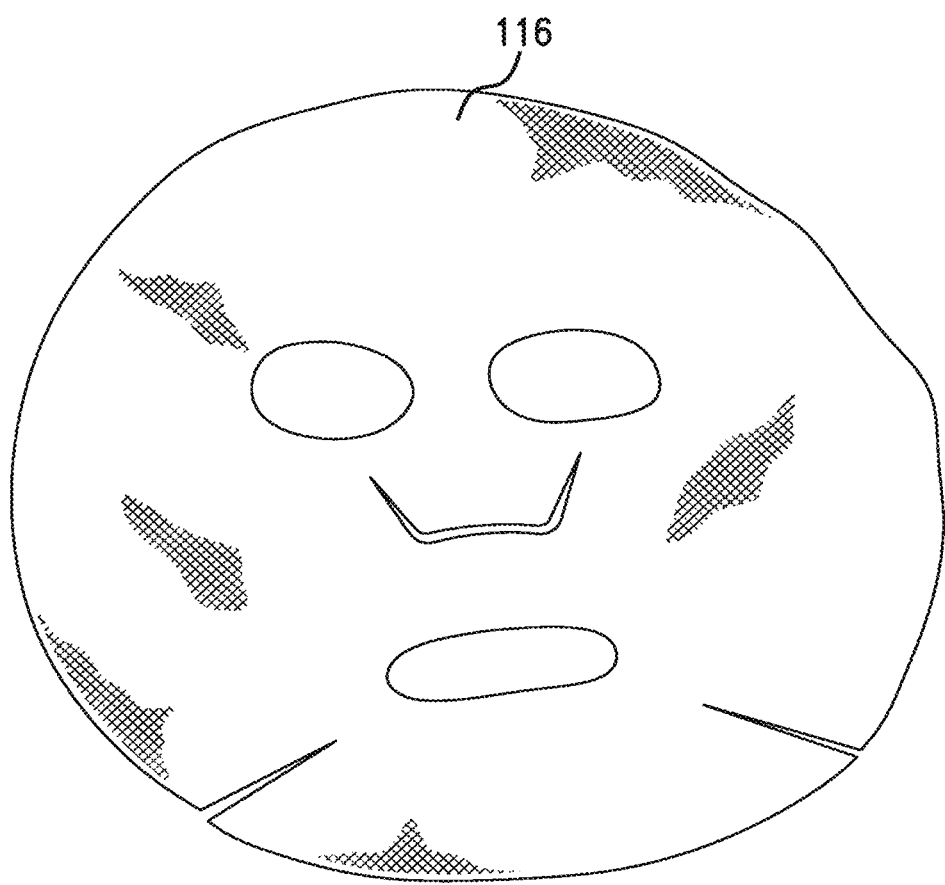
FIG. 3 is an illustration of the exemplary medium according to an exemplary embodiment of the present disclosure.

The medium 116 can be or can include a face mask, for example, as shown in FIGS. 1 and 3. In other exemplary configurations, the exemplary medium 116 can be or can include masks or applicators intended for use or application on other parts of the body, for example, the neck, leg, chest, etc., or can be a cloth or any other suitable vehicle.

Figure 4:
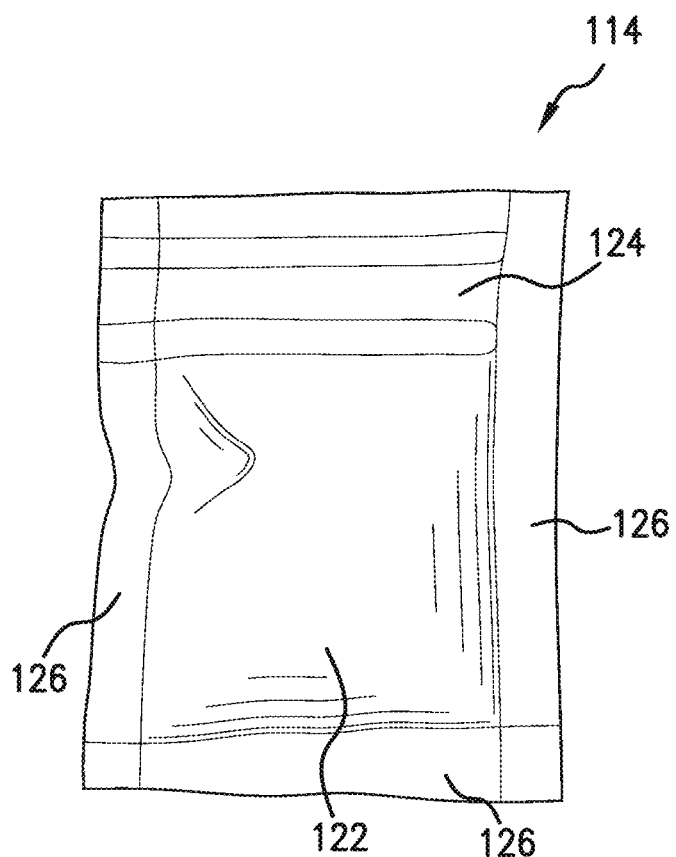
FIG. 4 is an illustration of the exemplary burstable structure according to an exemplary embodiment of the present disclosure.

Referring to FIG. 4, the cosmetic arrangement 110 can further include a pouch 114 that can be configured to store the exemplary solvent solution. The pouch 114 can be a burstable pouch that can be opened without the need to first open the packaging structure 112, which is described in further detail below.

For example, the pouch 114 can made of a single or multi-layered flexible plastic film that can be sealed together along or proximate to the edges of the pouch 114, for example, so as to form an inner area 122 in which the solvent solution can be contained. In certain exemplary, non-limiting configurations, the pouch 114 can be made of two layered flexible films. The outer layer can be, for example, a 48 gauge coated polyester bins, and the inner layer can be, for example, a 3 m polyethylene film. It is appreciated that other types of suitable films with other suitable film gauges can be used.

At least one edge of the pouch 114 can have a burst or frangible seal 124, and the remaining edges 126 can be heat sealed or thermally closed together. The frangible seal 124 can be an adhesive material with a high barrier sealant. The frangible seal 124 can be sufficiently strong to provide a strong resistance to pressure and force during the normal shipping, storage, and handling of the cosmetic arrangement 110 in order to prevent unintentional rupture of the frangible seal 124. At the same time, the frangible seal 124 can yield to, for example, a pressure applied with an intention to rupture the seal and expel the solvent solution from the pouch 114. In some exemplary configurations, the amount of pressure to be applied to cause the frangible seal 124 to rupture can range from, for example, approximately 0.2 lbs. to approximately 15 lbs. For example, in some configurations, the amount of pressure applied to cause the frangible seal 124 to rapture can be approximately 11.5 lbs. The heat sealed edges 126 can have a stronger bond to each other and a higher threshold against force and pressure than the frangible seal 124, such that the heat sealed edges 126 do not rupture when the frangible seal 124 can be caused to rupture by the user.

To open the pouch 114 containing the solvent, sufficient pressure can be applied to the pouch 114. The user can create sufficient pressure by, for example, holding the pouch 114 between his/her fingers, and squeezing his/her fingers together against the pouch 114. As the pressure can be applied to the pouch 114, the solvent solution and entrapped air, if any, can be pushed against the sealed edges 122, including the frangible seal 124, until the force of the solvent solution and entrapped air, if any, against the frangible seal 124, can cause the frangible seal 124 to break. The remaining sealed edges 122 can be bonded/sealed to each other in a stronger manner than that of the fringe seal 124 so that they remain intact.

Figure 2C:
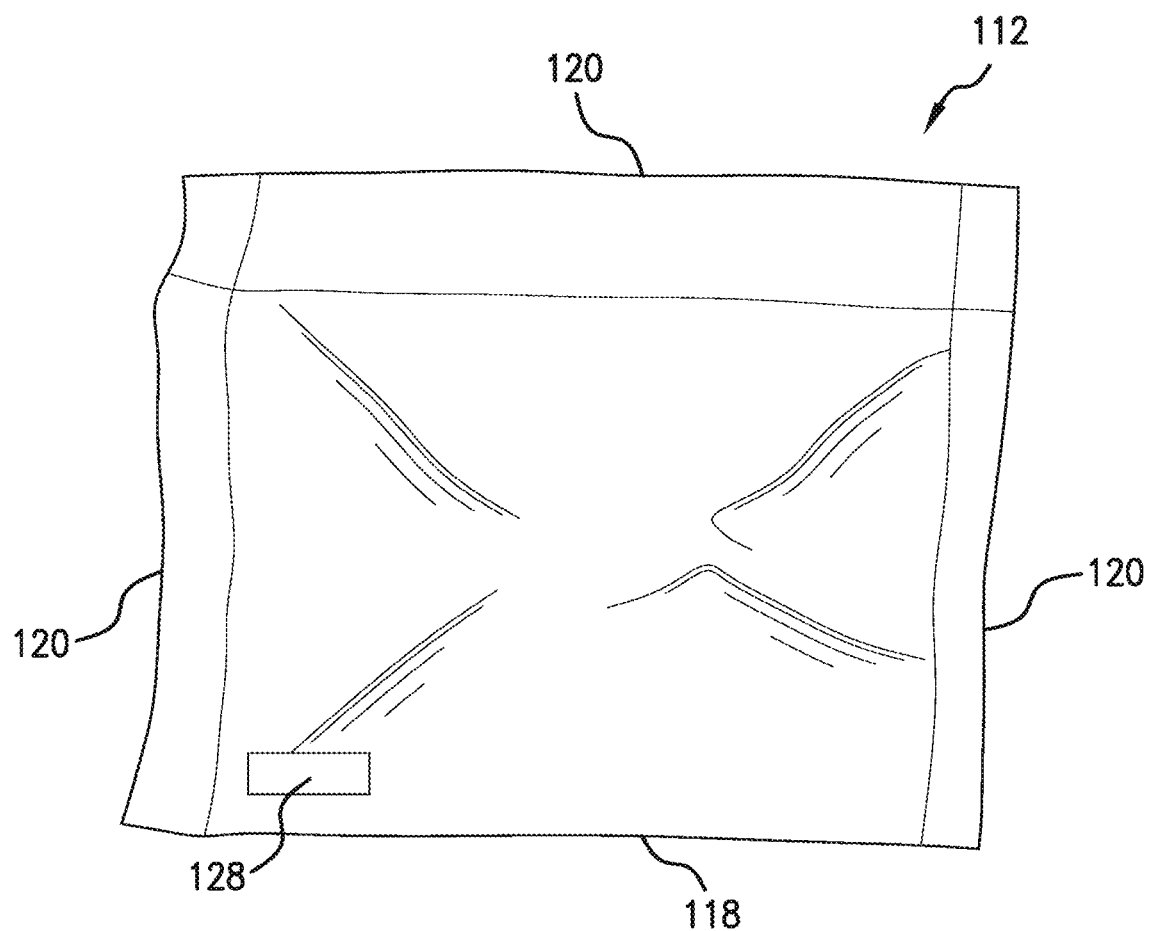
FIG. 2C is an illustration of the exemplary packaging structure including an exemplary indicator according to an exemplary embodiment of the present disclosure.

In certain exemplary configurations, the packaging structure 112 can include at least one indicator 128 on the exterior surface of the packaging structure 112 that can be easily visible to the consumer such as the indicator illustrated in FIG. 2C. The exemplary indicator(s) 128 can be configured to detect a liquid/fluid/powder leakage from the pouch 114 or a premature mixing of the active ingredients with the solvent solution. Such exemplary indicator(s) 128 can alert the user if the product is defective before purchasing and/or using the product. In some exemplary configurations of the present disclosure, the indicator(s) 128 can also be configured to detect a thorough mixing of the active ingredient with the solvent solution to signal to the user that the cosmetic arrangement 110 can be ready for use. In yet other exemplary configurations, the indicator 128 can detect both liquid/fluid/powder leakage from the punch 114 and the thorough mixing of the active ingredients and the solvent solution.

In some exemplary configurations of the present disclosure, the indicator(s) 128 can be a non-toxic, non-hazardous, and environmentally friendly agent that can react to the exemplary solvent solution within the pouch 114. In other exemplary configurations, the indicator(s) 128 can be or can include a pH indicator strip that can change color when the active ingredient mixes with the solvent solution. For example, when the Vitamin C can be mixed with the solvent solution, the pH indicator strip (e.g., the indicator 128) can change color, such as blue, to indicate that the Vitamin C has mixed with the solvent solution.

Alternatively or in addition, a window area can be used as a past of an indicator system/indicator 128. The packaging structure 112, in some exemplary configurations, can include the window area made of a clear material that can facilitate a user to view the interior space of the packaging structure 112. The window area can be small enough to prevent overexposure of the solvent and solvent to light, but large enough to facilitate a user to view the interior space of the packaging structure 112. The user can use the window area to determine whether the pouch 114 had been prematurely broken, or the user can use the window area to determine whether the active ingredients have mixed with the solvent solution. In some exemplary configurations, a pH indicating agent can cause the resulting mixture of the cosmetic active ingredient and solvent solution to change color and this change of color can be seen through the window area by the user. In further exemplary configurations, the medium 116 itself can contain a pH indicating agent, and the medium 116 can change color when it can be coated with the mixture of cosmetic active ingredient and solvent solution. The pH indicating agent can be in a powder form that can be loosely mixed within the cosmetic active ingredient, or in other exemplary configurations, the pH indicating agent can be a pH strip that can be viewed through the window area. Other suitable indicator and indicator systems can also be used.

Figure 5:
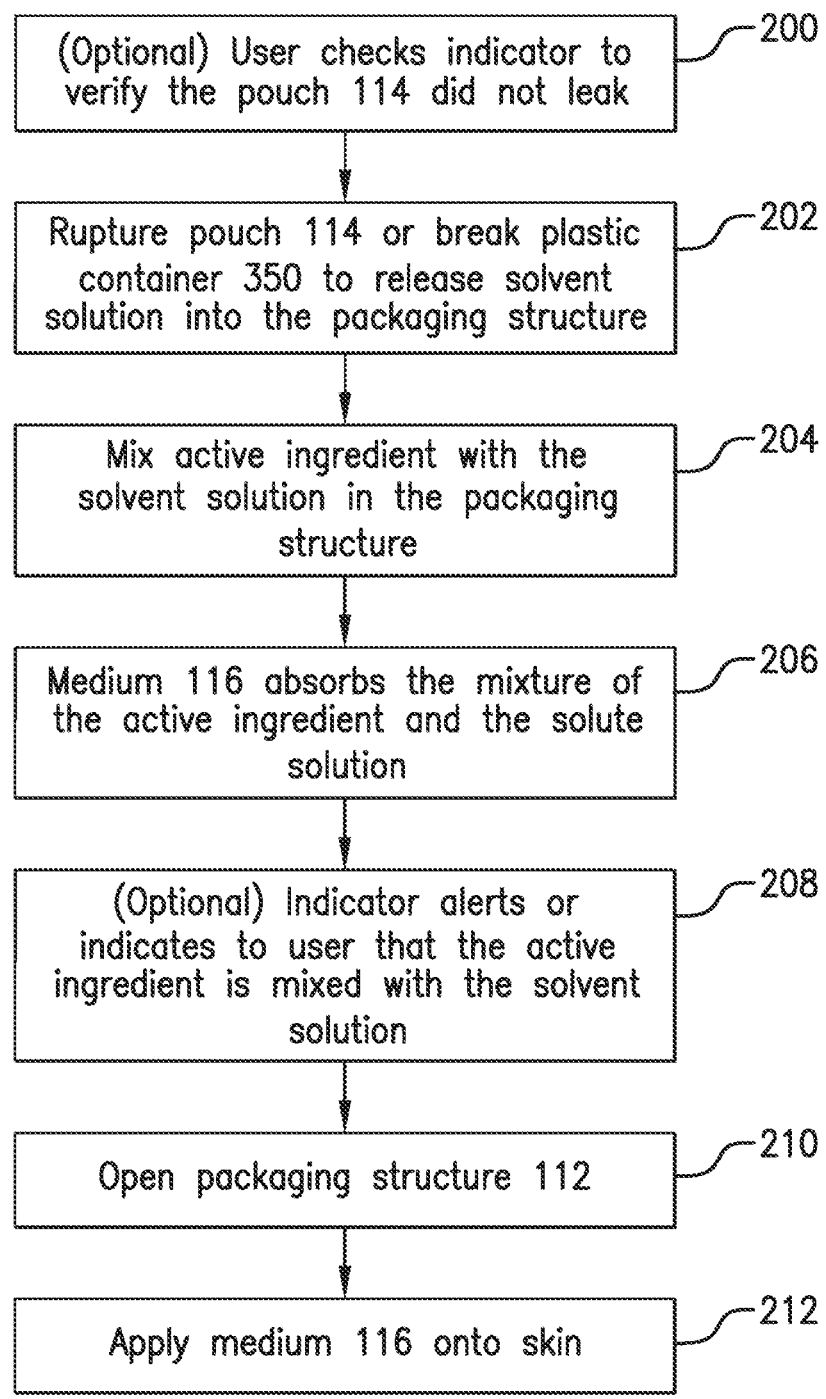
FIG. 5 is an exemplary flow diagram illustrating an exemplary method for using the exemplary cosmetic arrangement according to an exemplary embodiment of the present disclosure.

FIG. 5 illustrates at exemplary method for using the cosmetic arrangement 110. First, if the indicator 128 is provided, the user can check the indicator 128 to verify that the pouch 114, or the plastic container (e.g., a stick 350 from FIG. 8A), has not leaked (e.g. procedure 200). Before opening the packaging structure 112, the user can then effectuate a rupture of the pouch 114, or break the plastic container (e.g. stick 350) to expel the solvent solution into the packaging structure 112 (e.g., procedure 202). The user can rupture the pouch 114 by holding the pouch 114 between two fingers and pressing the fingers together and against the pouch 114. Other suitable methods of rupturing the pouch 114 can also be applied. For example, the pouch 114 can be squeezed in the palm of a user's hand. As pressure can be applied, the solvent solution and the entrapped air can press against the frangible seal 124 until the frangible seal 124 breaks. Alternatively, the user can break the container (e.g., stick 350). For example, the user can hold each end of the stick 350 in each hand and optionally have the user's thumbs placed about the perforation of the container to break the container. The user can then snap the stick, optionally at the perforated or weakened area. The user can then mix the cosmetic active ingredient with the solvent solution so that the active ingredient can sufficiently dissolve in the solvent (e.g., procedure 204). Mixing can be performed, for example, by shaking the packaging structure 112. The cosmetic mixture of the active ingredient and the solvent solution can then be absorbed by the medium 116 which can be contained in the packaging structure 112 (e.g., procedure 206). The user can facilitate absorption, of the medium 116 by shaking the packaging structure 112 or massaging the packaging structure 112, medium 116, and the mixture of cosmetic active ingredient and solvent solution, for example, with the user's fingers and/or hand(s). If the indicator 128 is provided, the user can check the indicator to verify that the cosmetic active ingredient and solvent solution have sufficiently mixed, and/or whether the medium 116 has sufficiently absorbed the mixture (e.g., procedure 208). The user can then open the packaging structure 112 (e.g., procedure 210) for example, at the separation arrangement, if provided, and apply the medium 116 onto the user's skin (e.g., procedure 212).

Exemplary results of an experiment of the dissolution of Vitamin C powder in water and absorption rate of the Vitamin C powder on the face mask medium are illustrated in section herein entitled "Experiment to dissolve Vitamin C powder."

Although the cosmetic arrangement 110 described herein has the solvent solution contained within the pouch 114 and the cosmetic active ingredient contained within the packaging structure 112, in alternative exemplary configurations, the solvent solution can be contained within the packaging structure 112 and the cosmetic active ingredient can be contained within the pouch 114. In such exemplary configurations, the pouch 114 can include sufficient entrapped air with the cosmetic active ingredient, particularly in cases where the cosmetic active ingredient can be in a powdered form, such that as pressure can be applied against the pouch 114, the entrapped air can be forced against the frangible seal 124, and to cause a rupture. In the case of plastic container, entrapped air may not be needed in order to break or snap the plastic container.

Figure 6:
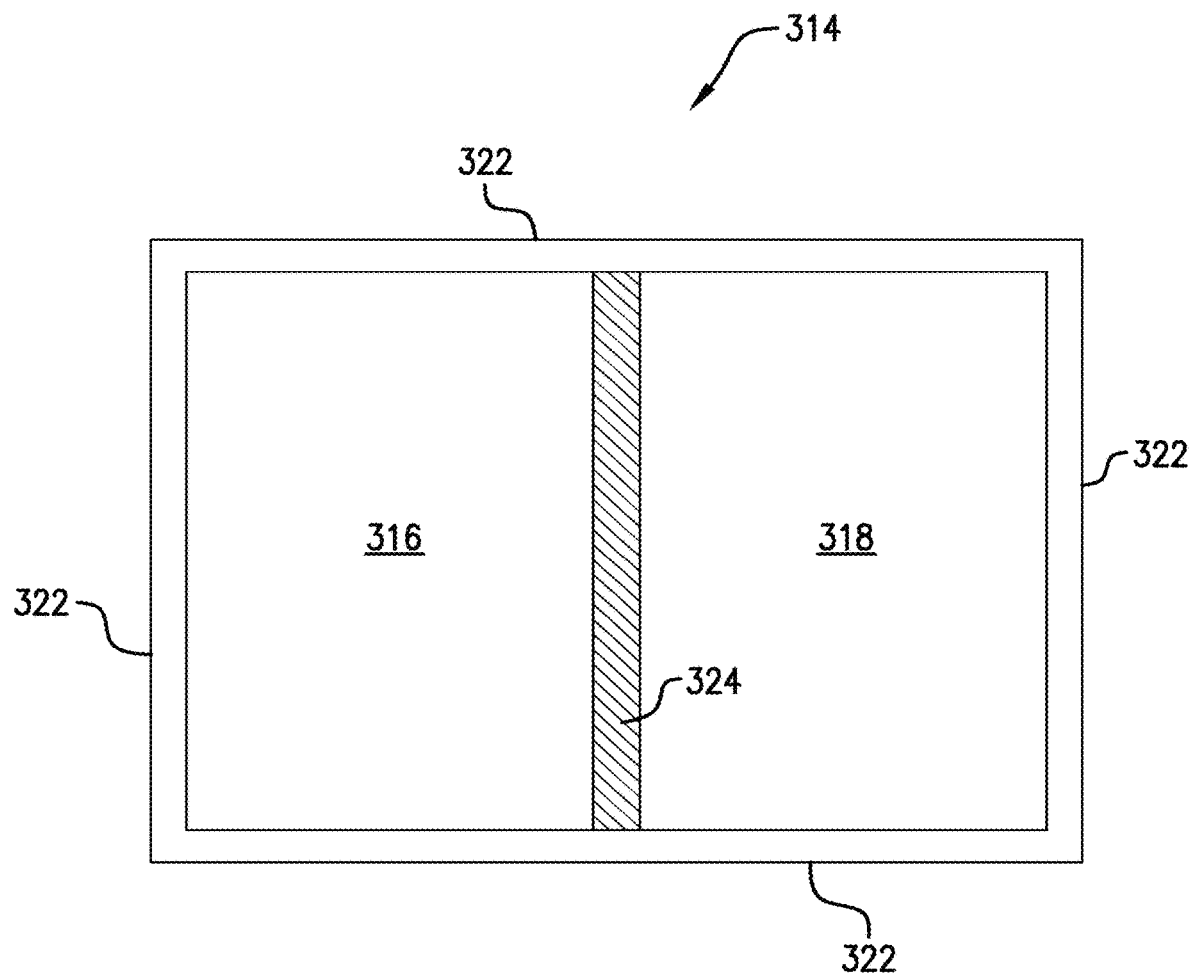
FIG. 6 is an illustration of an exemplary embodiment of the exemplary structure according to an exemplary embodiment of the present disclosure.

According to another exemplary embodiment of the cosmetic arrangement of the present disclosure as shown in FIG. 6, the pouch 314 can include at least two compartments 316 and 318 with a frangible seal 324 there between. The enter edges 323 of the pouch 314 can be heat sealed or thermally sealed together. For example, one compartment 316 can contain the solvent material and the other compartment 318 can contain the solvent solution. When the exemplary cosmetic arrangement is ready for use, the user can apply pressure to either one of the compartments 316 and 318 to cause the frangible seal 324 positioned therebetween to rupture open. Once ruptured, the solvent can be mixed with and dissolved in the solvent solution.

Figure 7:
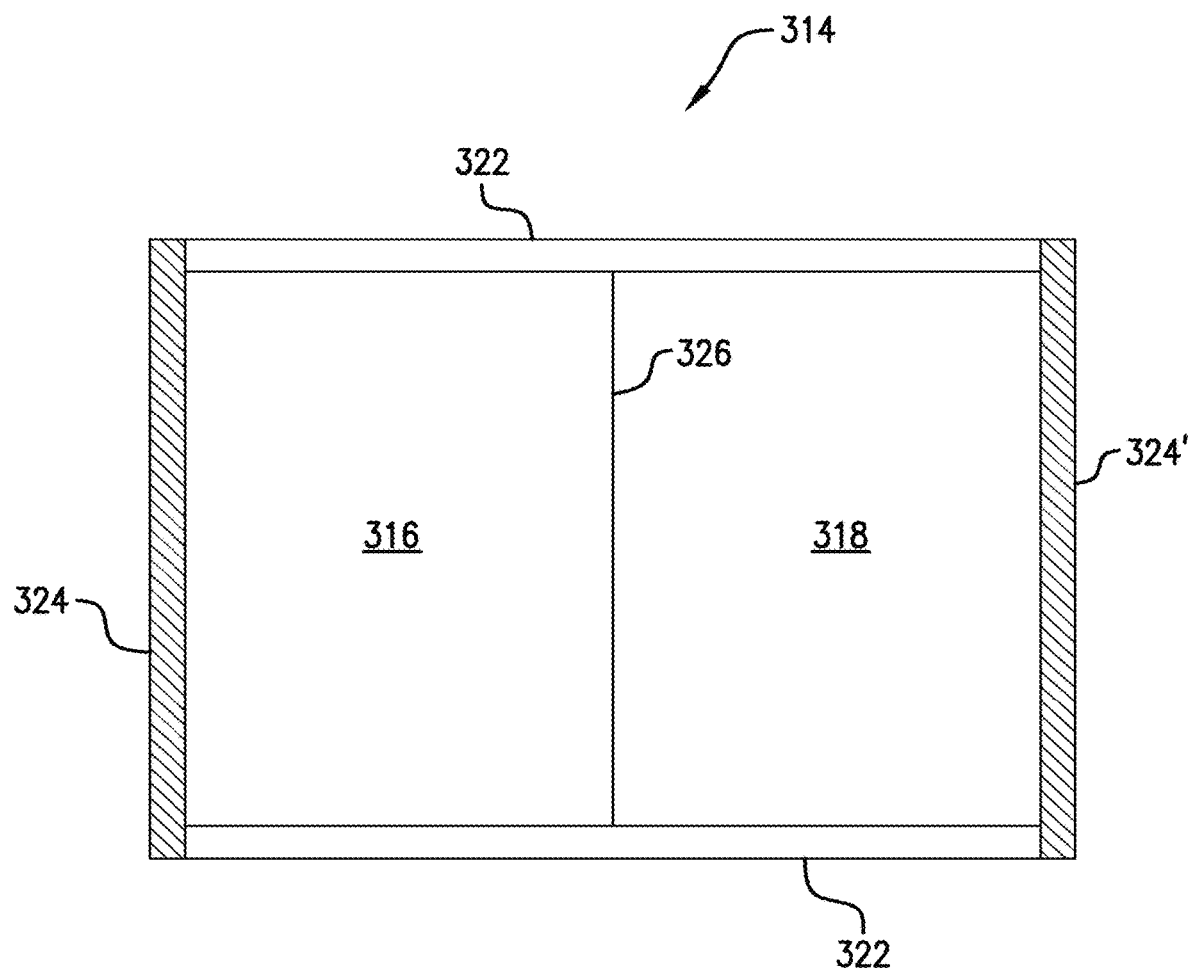
FIG. 7 is an illustration of a further exemplary embodiment of the exemplary burstable structure according to an exemplary embodiment of the present disclosure.

In other exemplary configurations, for example, as illustrated in FIG. 7, the pouch 314 can include compartments 316 and 318 with a heat sealed seal 326 therebetween, and at least two frangible seal 324, 324' can be positioned on the outer edges of the compartments 316, 318. The remaining outer edges 322 can also be heat-sealed together. When the exemplary cosmetic arrangement can be ready for use, the user can apply pressure to the compartments 316 and 318 to cause the frangible seals 324 and 324' to rupture and open. The solvent and solvent solution can then be expelled into the packaging structure 312, where they can be mixed together and absorbed into the medium 116.

Alternatively or in addition, for example, the pouch 314 including the compartments 316 and 318 can be used independently from the packaging structure 112 and/or the cosmetic arrangement 110 described herein. The compartment pouch 314 can be used to store other types of cosmetic products that do not need a medium. For example, the compartment pouch 314 can be used to store the active ingredients and solvent solution, respectively, of a face or body lotion, such as anti-aging lotion. Similar to the cosmetic masks described herein, the cosmetic active ingredients (e.g., anti-oxidant) in anti-aging lotion can degrade and lose their effectiveness over time, and thus, can benefit from the two compartment pouch structure described herein above.

In yet other exemplary configurations of the present disclosure, the pouch 114 can have more than two compartments. For example, the pouch 114 can have three or more compartments with the frangible seal between each pouch 114 and/or at the outer edges of the pouch 114.

Figure 8A:
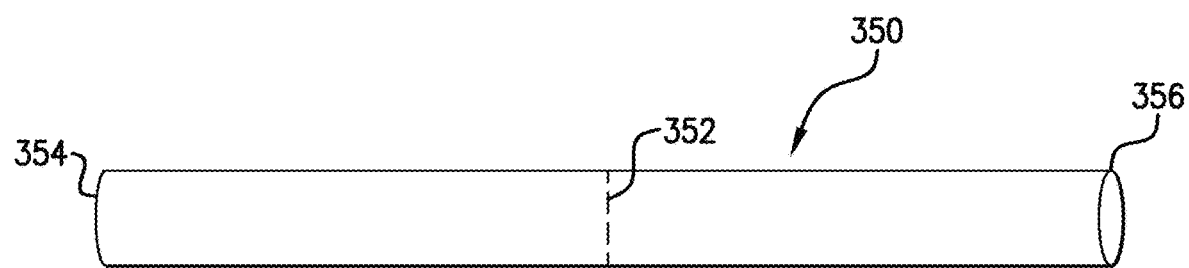
FIG. 8A is an illustration of an exemplary embodiment of an exemplary container according an exemplary embodiment of the present disclosure.
Figure 8B:
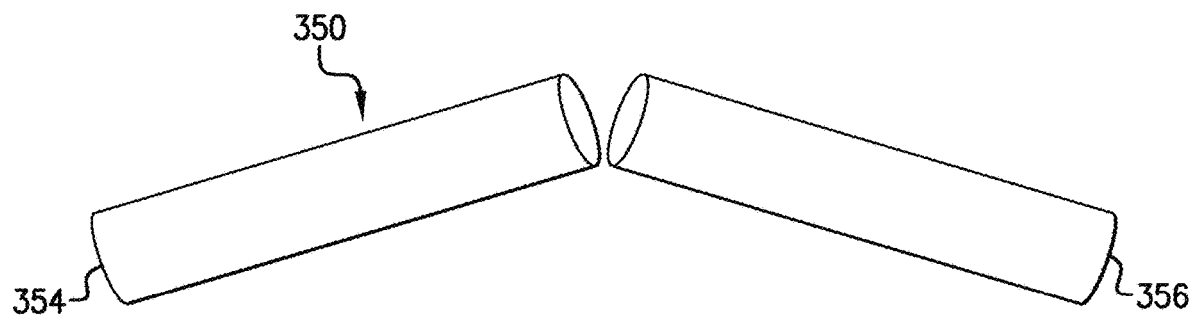
FIG. 8B is a further illustration of the exemplary embodiment of the exemplary container of FIG. 8A according to an exemplary embodiment of the present disclosure.

According to another exemplary embodiment of the exemplary cosmetic arrangement, the exemplary pouch 114 can be an exemplary container 350 (e.g., made of plastic or another suitable material), as illustrated in FIGS. 8A and 8B. The exemplary plastic container 350 can be made of a rigid, semi-rigid and/or inflexible plastic material. The plastic container material can be or include PolyEthylene Terephthalate Glycol ("PETG"). The length of the plastic container can range from about 2 inches to about 12 inches, with preferred length being at about 4 to 6 inches, although other suitable lengths can be used. The outer diameter of the plastic container can range term about 0.2 inches to about 1.3 inches, with the preferred diameter being from about 0.445 to about 0.742 inches, and with the most preferred diameter at about 0.572 inches, although other suitable diameters can be used. The thickness of the container can ranges from about 0.01 to about 0.1 inches, with the preferred thickness being about 0.022 inches, although other suitable thicknesses can be need. The inner diameter of the plastic container can range from about 0.18 to about 1.43 inches, with a preferred diameter range being front about 0.4 to about 0.53 inches, although other suitable diameters can be used. The color of the plastic container can be clear, opaque and/or colored. The plastic container can be filled, heat sealed and/or capped after it has been filled with solvent.

As the exemplary plastic container 350 can be made of a rigid, semi-rigid, and/or inflexible plastic material, this can reduce unintentional rupturing of the plastic container 350 before reaching the bands of the user. The plastic container 350 can be advantageous, as, for example, the plastic container 350 can be less bulky than a pouch. A bulky structure can prevent close or tight packing of the overall package in a box for storage or shelf display. This can be alleviated by the rigid, semi-rigid and/or inflexible plastic material.

Figure 8C:
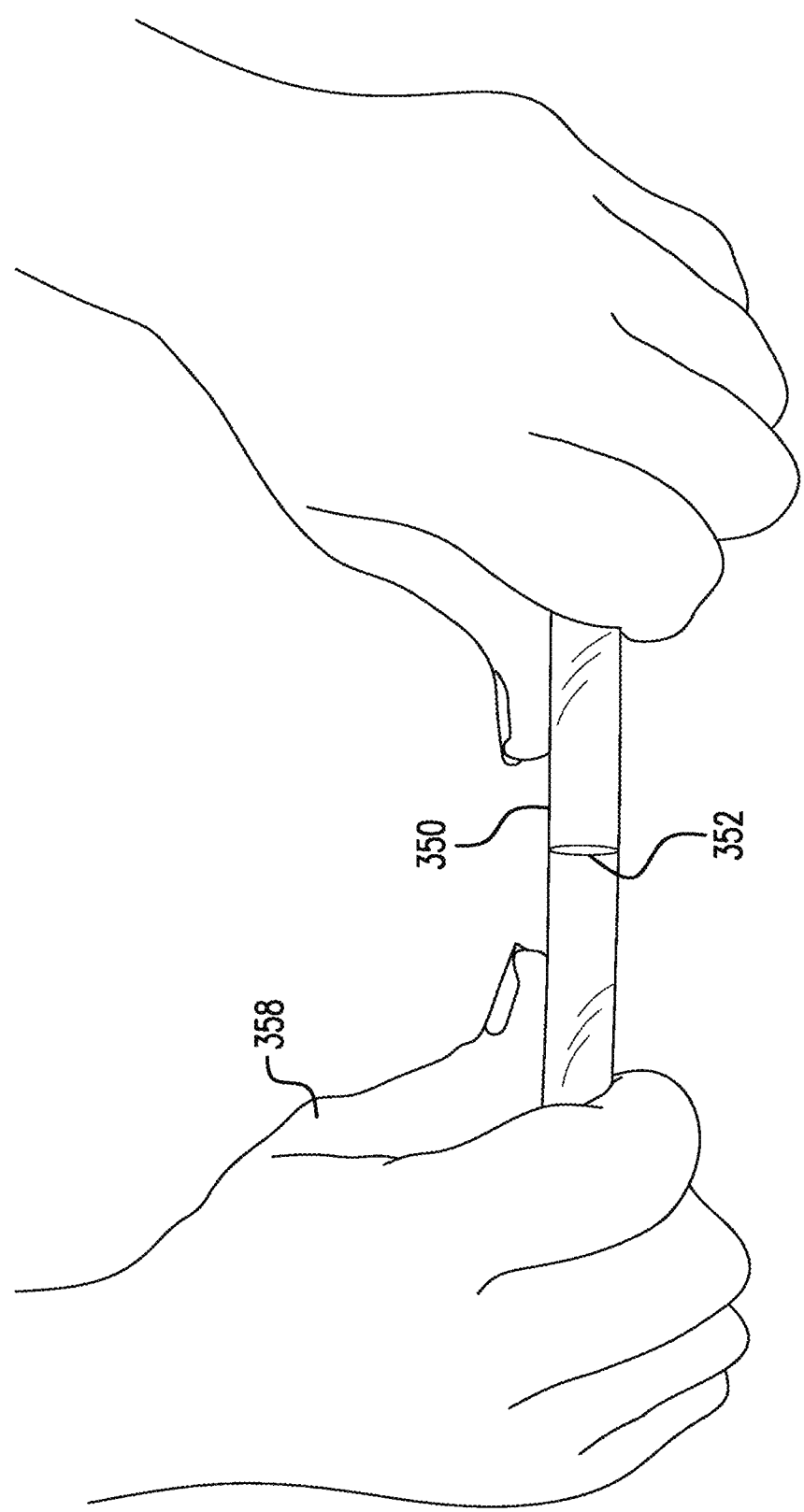
FIG. 8C is an even further illustration of the exemplary container shown in FIG. 8A being held in order to break the plastic container according to an exemplary embodiment of the present disclosure.

The exemplary plastic container 350 can be a plastic tube and, in some configurations, can be in the shape of a rectangle or a rod. It is appreciated that the plastic container 350 can be of other suitable shapes. The exemplary plastic container 350 can include a linear, pre-scored, exemplary perforation 352 that can be placed across or around the sides of the plastic container 350. The exemplary perforation 352 can be in the midline of the container, although in some configurations, the perforation 352 can be positioned on other suitable locations on the plastic container 350. The exemplary plastic container 350 can be configured to contain the solvent solution such that the solvent solution can be maintained separately from the solute. To mix the active ingredients with the solvent solution, the plastic container 350 can be snapped or broken along the perforation 352 by the user. In some configurations, the plastic container 350 can be snapped or broken in half along the perforations 352. The user can hold each end 354 and 356 of the plastic container 350 in each hand (e.g., hand 358) and optionally have the user's thumbs placed about the perforation 352 (see e.g., FIG. 8C). The user can then bend the two ends 354 and 356 of the exemplary plastic container 350 causing the plastic container to break at the exemplary perforation 352.

Other suitable methods of breaking or snapping the plastic container 350 can also be used. FIG. 8A illustrates the exemplary plastic container 350 in an unbroken configuration and FIG. 8B illustrates, the exemplary plastic container 350 in a broken configuration. The plastic container 350 can be an audible sound associated with breaking the plastic container; this can be an additional cue to the user that solvent in this plastic tube has been released. In contrast, pouch 114 configuration, the sound associated with bursting the pouch may not be audible. Second, it can be easier to locate the long elongated plastic container in the sealed package structure 112 because of its well defined and outlined shape and tactile texture (e.g., firm). Moreover, it can be easy to break the plastic container using a snap-like action with two hands.

Figure 9:
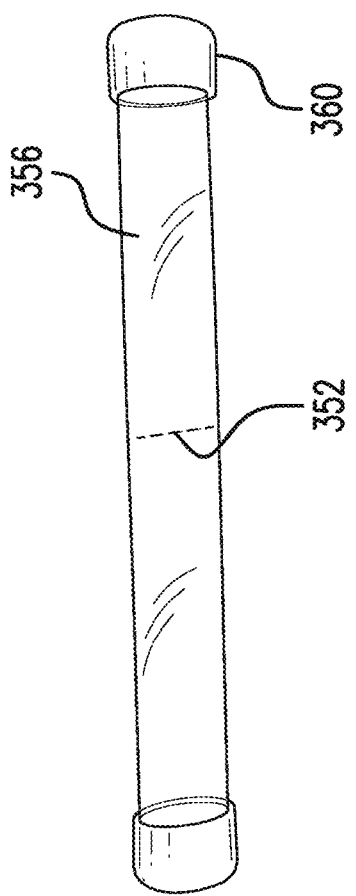
FIG. 9 is an illustration of a yet further exemplary container according to an exemplary embodiment of the present disclosure.

The plastic container can also be a uniformly thick cylindrical tube, without any perforations, (see e.g., a plastic tube 356 of FIG. 9), and the liquid or solvent inside of plastic tube 356 can be maintained within plastic tube 356 through end caps 360. End caps 360 can be removeably attached to the plastic tube 356. When the user wishes to gain access to the solvent, the user can remove one or both of the end caps 360, and pour the solvent out of plastic tube 356. In addition, plastic container 356 of FIG. 9 can also have perforation 352 to facilitate breaking of plastic container 356 in addition to, or in alternative of removing end caps 360.

Figure 10:
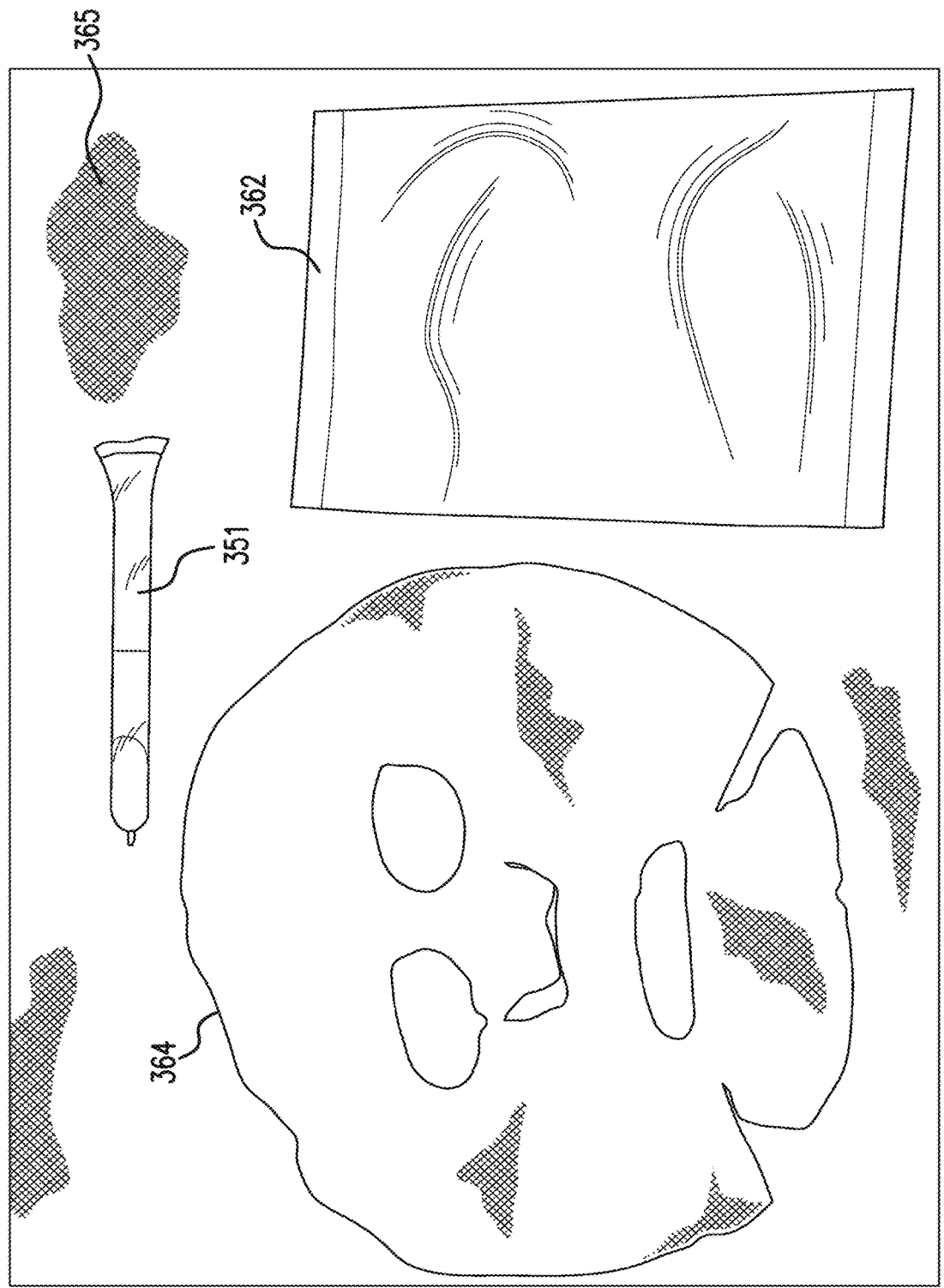
FIG. 10 is at illustration of an exemplary cosmetic arrangement which can include packaging structure (e.g., including ingredients), medium, and a breakable container according to an exemplary embodiment of the present disclosure.

FIG. 10 shows a cosmetic arrangement 365 that can include an exemplary medium 364 (e.g., a mask) that can act as a delivery vehicle for the various cosmetic active ingredients. The exemplary medium 364 can be made of a material such as paper, cotton fabric, cellulous and/or hydrogel, which can be configured to absorb the mixture of the cosmetic active ingredients and solvent solution, and deliver this mixture to a person's skin. As described above, the cosmetic active ingredient and medium 364 can both be contained in the packaging structure 362. The cosmetic arrangement 365 can further include the plastic container 350 that can be configured to store the exemplary solvent solution. The plastic container 350 can be either a snapable plastic container (e.g., plastic container 350) and/or a plastic container 351 can have removable ends (e.g., the plastic container 356).

Figure 11:
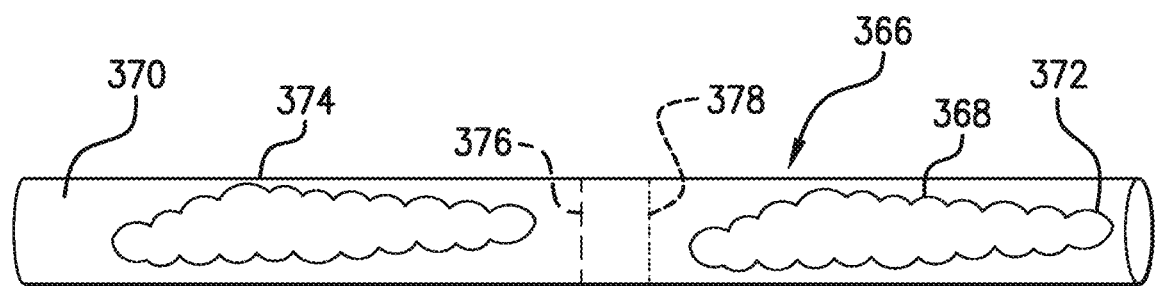
FIG. 11 is an illustration of a further breakable container according to an exemplary embodiment of the present disclosure.

FIG. 11 illustrates a further breakable plastic container (e.g., plastic container 366) according to another exemplary embodiment of the present disclosure. The plastic container 350 can include two (2) compartments 370 and 372 each with its own liquid, solvent and/or other cosmetic active or inactive ingredient (e.g., cosmetic ingredients 368 and 374. Exemplary compartments 370 and 372 can be separated by a wall 376, which can maintain the cosmetic ingredient in its respective compartment. The wall 376 can be weakened or designed such that pressure by a user on the wall 376 can cause the wall 376 to break, facilitating the mixture of cosmetic ingredients 368 and 374. Thus, the cosmetic ingredients 368 and 374 can be separately maintained to preserve the efficacy of each cosmetic ingredient until the user uses the cosmetic ingredients. After the user breaks the wall 376, and cosmetic active ingredients 368 and 374 have been combined, the user can break the plastic container 366 using an exemplary weakened area or perforation 378, similar to the perforation 352 described above, to facilitate the removal of the combined active ingredient from the plastic container 366. Thus, the plastic container 378 is an easy to use, portable cosmetic ingredient holder that can separately maintain two or more cosmetic ingredients until the users wants to apply the combined active ingredient.

Although the exemplary arrangement 110 and the exemplary embodiments of the plastic containers 350, 367, 378 are described herein using cosmetic active ingredients, the arrangement 110 the exemplary embodiments of the plastic containers 350, 367, 378 are not limited to cosmetic active ingredients, and the arrangement can be used with other types of ingredients.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances. Further, to the extent that the prior art knowledge has not been explicitly incorporated by reference herein above, it is explicitly incorporated herein in its entirety. All publications referenced are incorporated herein by reference in their entireties.

Various components of the exemplary storage arrangement can include any number of dimensions, and the Figures provided herein illustrate exemplary sets of dimensions for certain exemplary embodiments of the present disclosure. Other dimensions, for example for other exemplary embodiments, are also possible.

Any and all references specifically identified in the specification of the present application are expressly incorporated herein in their entirety by reference thereto. The term "about" and "approximately" as used herein, should generally be understood to refer to both the corresponding number and a range of numbers. Moreover, all numerical ranges herein should be understood to include each whole integer within the range.

What is claimed is:

1. An arrangement comprising:
   a first structure enclosing at least one cosmetic active ingredient;
   a second structure enclosing a solvent solution;
   at least one third structure separating the solvent solution from the at least one cosmetic active ingredient;
   a medium configured to absorb a mixture of the at least one cosmetic active ingredient and the solvent solution; and
   a visual indicator structure located on a surface of the arrangement configured to visually indicate whether the at least one cosmetic active ingredient and the solvent solution have come in contact with one another, wherein the visual indicator structure includes at least one of:
     a pH agent associated with the at least one cosmetic active ingredient and the solvent solution, and wherein, when the at least one cosmetic active ingredient and the solvent solution come into contact with each other, the pH agent is configured to change color, or
     a non-toxic and non-hazardous agent that is configured to react with the mixture of the at least one cosmetic active ingredient and the solvent solution upon a contact therewith, and produce an indication that the at least one cosmetic active ingredient and the solvent solution have been mixed,
   wherein, upon an application of a particular amount of pressure on at least one portion of the arrangement, the at least one cosmetic active ingredient and the solvent solution are caused to come into contact with one another.

2. The arrangement of claim 1, wherein the first, second and third structures form a single unitary structure with the at least one third structure provided between the first and second structures.

3. The arrangement of claim 2, wherein the pressure applied against at least one of the first structure or the second structure causes the at least one third structure to rupture so as to expose the at least one cosmetic active ingredient to the solvent solution, and mix the at least one cosmetic active ingredient with the solvent solution.

4. The arrangement of claim 1, wherein:
   the second structure is contained within the first structure, and
   the second structure further includes the at least one third structure, wherein, upon the application of the pressure against the second structure, the at least one third structure ruptures causing the solvent solution to be expelled from the second structure and come into contact with the at least, one cosmetic active ingredient in the first structure.

5. The arrangement of claim 1, wherein the particular amount of the pressure applied on the second structure is between approximately 0.2 lbs. to approximately 15 lbs.

6. The arrangement of claim 1, wherein the medium is configured to absorb the mixture of the at least one cosmetic active ingredient and solvent solution after the at least one third structure is caused to rupture.

7. The arrangement of claim 1, further comprising a clear window area on the first structure that facilitates an external view of an interior space of the first structure.

8. The arrangement of claim 1, wherein the first structure is substantially opaque to at least one of prevent or reduce an amount of light exposure to the at least one cosmetic active ingredient and the solvent solution.

9. The arrangement of claim 1, wherein the at least one cosmetic active ingredient includes an anti-oxidant.

10. An arrangement comprising:
    a first structure enclosing at least one cosmetic active ingredient;
    a second structure enclosing a solvent solution;
    a medium configured to absorb a mixture of the at least one cosmetic active ingredient and the solvent solution; and
    a visual indicator structure located on a surface of the arrangement, and configured to visually indicate whether the at least one cosmetic active ingredient and the solvent solution have come in contact with one another,
    wherein, upon an application of a particular amount of pressure on at least one portion of each of the first structure and the second structure, the at least one cosmetic active ingredient and the solvent solution are caused to come into direct contact with one another, and
    wherein the visual indicator structure includes:
      a. a pH agent associated with the at least one cosmetic active ingredient and the solvent solution, and wherein, when the at least one cosmetic active ingredient and the solvent solution come into contact with each other, the pH agent is configured to change color, or b. a non-toxic and non-hazardous agent that is configured to react with the mixture of the at least one cosmetic active ingredient and the solvent solution upon a contact therewith, and produce an indication that the at least one cosmetic active ingredient and the solvent solution have been mixed.

* * * * *